United States Patent [19]

Leichnitz

[11] 4,259,287

[45] Mar. 31, 1981

[54] TESTING TUBE CONSTRUCTION FOR MEASURING SODIUM HYDROXIDE AND/OR CALCIUM OXIDE

[75] Inventor: Kurt Leichnitz, Grönau, Fed. Rep. of Germany

[73] Assignee: Drägerwerk Aktiengesellschaft, Fed. Rep. of Germany

[21] Appl. No.: 88,125

[22] Filed: Oct. 25, 1979

[30] Foreign Application Priority Data

Dec. 22, 1978 [DE] Fed. Rep. of Germany ....... 2855648

[51] Int. Cl.³ ............................................. G01N 31/22
[52] U.S. Cl. ................................... 422/59; 23/232 R; 252/408; 422/60
[58] Field of Search .................... 23/230 R, 232 R; 422/58, 59, 60; 252/408

[56] References Cited

U.S. PATENT DOCUMENTS 3,131,030  4/1964  Grosskopf ............................. 422/59
3,312,527  4/1967  McConnaughey ..................... 422/60

OTHER PUBLICATIONS

L. Pauling, "General Chemistry", 2nd Edition, pp. 374–375, W. H. Freeman, San Francisco, 1953.
L. F. Hamilton et al., "Calculations of Analytical Chemistry", p. 190, McGraw-Hill, New York, 1947.
Chemical Abstracts, 86: 95109e (1977).
"Standard Methods of Chemical Analysis," 6th Edition, vol. 2, Frank J. Welcher, ed., p. 256, D. Van Nostrand Co., Inc., Princeton, 1963.

*Primary Examiner*—Sidney Marantz
*Attorney, Agent, or Firm*—John J. McGlew

[57] ABSTRACT

A testing tube for measuring sodium hydroxide and/or calcium oxide aerosols, comprises, a glass tube having breakoff points at each end to open at each end and containing a front layer of a substrate material impregnated with ammonium chloride and a following indicating layer of a substrate material impregnated with an acid and bromphenol blue.

3 Claims, 1 Drawing Figure

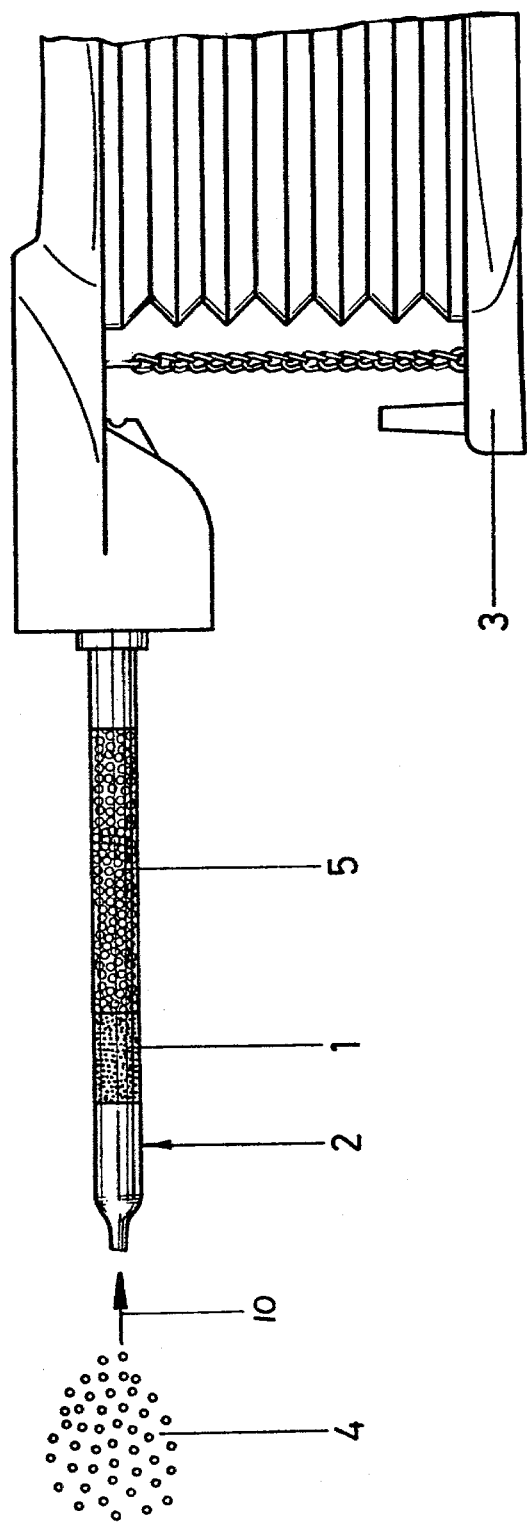

TESTING TUBE CONSTRUCTION FOR MEASURING SODIUM HYDROXIDE AND/OR CALCIUM OXIDE

FIELD AND BACKGROUND OF THE INVENTION

This invention relates to gas-testing devices in general and, in particular, to a new and useful testing tube for measuring sodium hydroxide and/or calcium oxide aerosols.

Testing tubes for the quantitative determination of NaOH and/or CaO aerosols have not been heretofore. The reason for this lies in the unclear reaction behavior of the aerosols in the indicating preparations of the testing tubes.

A known method for detecting both volatile and misty arsines uses a testing tube in which filter of inorganic or organic fibrous materials, such as glass-wool, cellulose, or asbestos, is arranged in front of a highly active silica gel layer.

When an air sample is passed through, arsine mists contained therein are retained in the filter, while volatile arsines are fixed by the silica gel. Subsequently, a reagent in the form of a solution of tin-(2)-chloride in concentrated hydrochloric acid is introduced into the testing tube. The mist particles retained by the fiber filter are entrained by the reagent and are flushed toward the silica gel layer. They react with the reagent only on the silica gel in the form of an arsenic deposit. The reaction is thus always observed in the silica gel layer on the silica gel, regardless of whether arsine mists or volatile compounds are present. The reaction takes place directly between the substances to be detected and the indicating reagent. The activity of the silica gel plays a substantial part in the reaction processes. This measuring method can, therefore, only provide qualitative proof of the arsines. In addition, the application of the liquid reaction solution is not harmless (See German Pat. No. 742,689).

SUMMARY OF THE INVENTION

The present invention provides a testing tube with quantative indication for the measurement of NaOH and/or CaO aerosols.

In the known glass tube construction, the testing tube has a front layer and an indicating coat arranged behind it in the direction of flow of the gas to be measured. According to a simple solution of the invention, the front layer is impregnated with an activable reagent system. Aerosol is deposited in the front layer by a filter effect of the material of the front layer. After the deposit, it reacts with the reagent system, forming a readily volatile reaction product. The reagent system is now present in excess relative to the aerosol in a stoichiometric view of the reaction.

The amount of the readily volatile reaction product newly formed in the front layer, which is completely new with regard to the aerosol and was formed only from the reaction system, is proportional to the amount of reacted aerosol deposited in the front layer. The readily volatile reaction product flows to the following indicating layer, where it is measured by a known color reaction.

Accordingly, an object of the present invention is to provide a testing tube for measuring sodium hydroxide and/or calcium oxide aerosols which comprises a glass tube provided with breakoff points at each end to open the tube for flow of a gas to be tested therethrough and including a front layer in the tube in the direction of gas movement of a substrate material impregnated with ammonium chloride and a following indicating layer of a substrate material impregnated with acid and bromophenol-blue.

A further object of the invention is to provide a testing tube which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a side elevational view of an aerosol testing device, constructed in accordance with the present invention.

DESCRIPTION OF THE PREFERRED EMBODIMENT

Referring to the drawing in particular, the invention embodied therein, comprises, a testing device for testing the presence of aerosols for gases which are directed through an indicating tube, generally designated 2, which, in the embodiment shown, is a glass tube having a breakoff end at each end which is broken off to permit the flow of gases therethrough in the direction of an arrow 10.

The testing tube comprises the glass tube 2 having a first or front layer 1 and an indicating rear layer 5 arranged therein in the direction of flow of the gas to be measured. The gas sample to be measured, which can contain NaOH and/or CaO aerosols 4, is sucked by pump 3 into the glass tube, which is opened by breaking off the points or ends thereof. The gas-permeable front layer 1, which acts as a filter for the aerosols, consists of a substrate material, such as silica gel, glass fibers, etc., and is impregnated with ammonium chloride.

The NaOH and/or CaO aerosol contained in the gas sample reacts with the ammonium chloride after being deposited in front layer 1 (equation 1), forming ammonia. The ammonia, as a gaseous reaction product, then reacts in the indicating rear layer 5 with the reagents hydrochloric acid and bromphenol blue, which are already known for use with testing tubes, and the amount of the reaction product is measured.

The chemical course is represented in the following equations:

1—sorption NaOH— and/or CaO+front layer 1 with impregnation NH$_4$Cl

2—activation and reaction in front layer 1

$$NH_4Cl + NaOH \rightarrow NH_3 + NaCl + H_2O$$

$$2NH_4Cl + CaO \rightarrow 2NH_3 + CaCl_2 + H_2O$$

3—measurement in indicating layer 5 over the reaction product

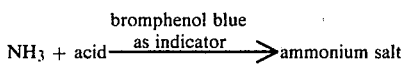

While a specific embodiment of the invention has been shown and described in detail to illustrate the application of the principles of the invention, it will be understood that the invention may be embodied otherwise without departing from such principles.

What is claimed is:

1. A testing tube, for quantitatively measuring sodium hydroxide and/or calcium oxide aerosols, comprising, a tube having an opening at each end for the flow of a gas to be tested therethrough, a front layer of material disposed in said tube comprising a substrate material impregnated with ammonium chloride and an indicating layer disposed behind the substrate material in respect to the direction of gas flow and comprising a substrate material impregnated with acid and bromphenol blue, said tube being made of glass and incuding breaking tips at each end which may be severed to open the tube, whereby stoichiometric quantities of the sodium hydroxide and/or calcium oxide of the gas to be tested react with the ammonium choride in the front layer to produce stoichiometric quantities of ammonia, the ammonia reacting with the acid in the presence of the bromphenol blue to indicate the stoichiometric and quantitative amount of ammonia produced which corresponds to the amount of sodium hydroxide and/or calcium oxide in the gas to be tested.

2. A testing tube as claimed in claim 1, wherein said front layer comprises a substrate material of silica gel or glass fibres, said substrate material being impregnated with ammonium chloride.

3. A testing tube, as claimed in claim 1, wherein said indicating layer comprises hydrochloric acid and bromphenol blue.

* * * * *